United States Patent
Martinez-Castro et al.

(10) Patent No.: US 10,131,605 B2
(45) Date of Patent: Nov. 20, 2018

(54) TRI-SUBSTITUTED AROMATIC-CONTAINING POLYMERIC DISPERSANTS

(71) Applicant: RHODIA OPERATIONS, Paris (FR)

(72) Inventors: Nemesio Martinez-Castro, Bristol, PA (US); Lichang Zhou, Lawrenceville, NJ (US); Eugene J. Anderson, Marlton, NJ (US); Brian Vest, Levittown, PA (US)

(73) Assignee: Rhodia Operations, Paris (FR)

(*) Notice: Subject to any disclaimer, the term of this patent is extended or adjusted under 35 U.S.C. 154(b) by 354 days.

(21) Appl. No.: 14/661,957

(22) Filed: Mar. 18, 2015

(65) Prior Publication Data

US 2015/0266980 A1    Sep. 24, 2015

Related U.S. Application Data

(60) Provisional application No. 61/954,857, filed on Mar. 18, 2014, provisional application No. 61/954,852, filed on Mar. 18, 2014.

(51) Int. Cl.

| | |
|---|---|
| C07C 41/03 | (2006.01) |
| C07C 43/205 | (2006.01) |
| C08F 22/12 | (2006.01) |
| C08K 3/04 | (2006.01) |
| C08K 5/13 | (2006.01) |
| C07C 69/54 | (2006.01) |
| C07C 37/14 | (2006.01) |
| C08F 20/30 | (2006.01) |
| C08F 220/30 | (2006.01) |

(52) U.S. Cl.
CPC .......... *C07C 43/2055* (2013.01); *C07C 37/14* (2013.01); *C07C 41/03* (2013.01); *C07C 69/54* (2013.01); *C08F 20/30* (2013.01); *C08F 22/12* (2013.01); *C08K 3/04* (2013.01); *C08K 5/13* (2013.01); *C08F 2220/306* (2013.01)

(58) Field of Classification Search
CPC ........ C08F 22/12; C08K 3/04; C07C 43/2055
See application file for complete search history.

(56) References Cited

U.S. PATENT DOCUMENTS

| | | | |
|---|---|---|---|
| 3,937,283 A | | 2/1976 | Blauer et al. |
| 4,579,670 A | | 4/1986 | Payne |
| 5,551,516 A | | 9/1996 | Norman et al. |
| 5,770,760 A | | 6/1998 | Robinson |
| 2009/0186968 A1 | * | 7/2009 | Zong ...................... C07C 43/23 524/131 |

FOREIGN PATENT DOCUMENTS

| | | |
|---|---|---|
| DE | 3407565 A1 | 9/1985 |
| EP | 0186255 A2 | 2/1985 |
| EP | 0177111 A2 | 4/1985 |
| EP | 0149173 A1 | 7/1985 |
| JP | 60229969 A2 | 11/1985 |
| JP | 61241370 A2 | 10/1986 |
| JP | 2004505127 A | 2/2004 |
| RU | 2246504 C1 | 2/2005 |
| WO | 0035863 A1 | 6/2000 |
| WO | 2013072696 A1 | 5/2013 |

OTHER PUBLICATIONS

G. Poehlen, "Emulsion Polymerization", Encyclopedia of Polymer Science and Engineering, vol. 6, pp. 1-51 (John Wiley & Sons, Inc., NY, NY, 1986).
A. S. Sarac, "Redox Polymerization", Progress in Polymer Science 24 (1999), pp. 1149-1204.
Edited by Raymond E. Kirk and Donald F. Othmer, Encyclopedia of Chemical Technology, Third Edition, John Wiley & Sons, vol. 16, pp. 248-273 (entitled "Nuts"), Copyright 1981.
"Oilfield Applications", Encyclopedia of Polymer Science and Engineering, vol. 10, pp. 328-366 (John Wiley & Sons, Inc., New York, NY., 1987).

* cited by examiner

Primary Examiner — Peter D. Mulcahy

(57) ABSTRACT

Disclosed are novel tri-substituted aromatic-alkoxylated polymeric dispersants and related method of preparing. Also disclosed are methods of dispersing at least one pigment comprising the following steps: contacting an aqueous solution containing at least one pigment with the polymeric dispersant copolymers as described herein.

20 Claims, 1 Drawing Sheet

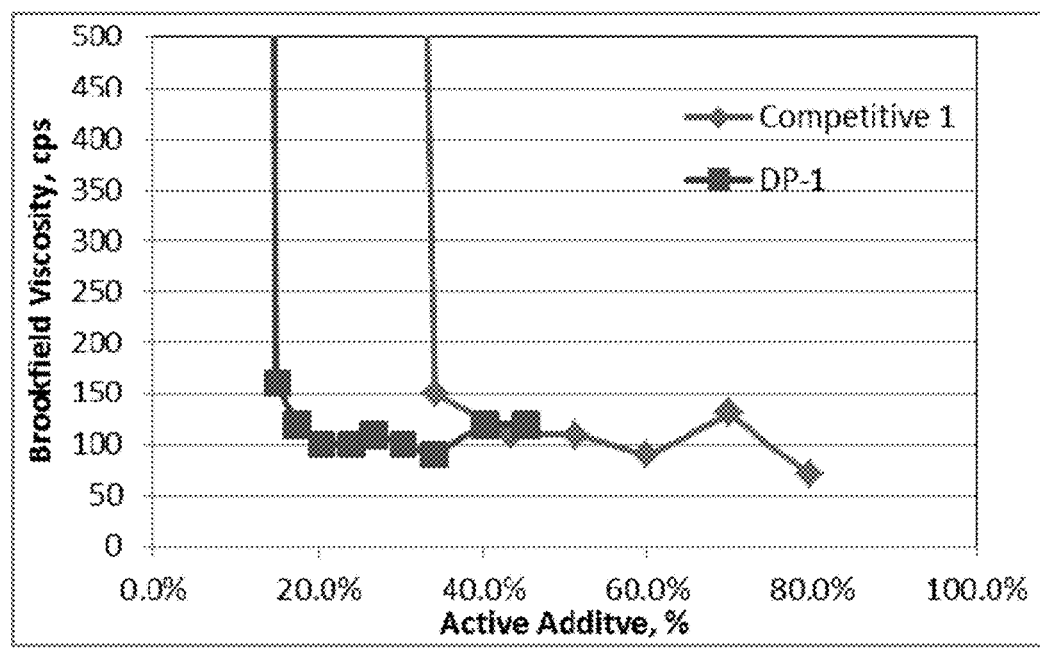
Dispersant demand curve

TRI-SUBSTITUTED AROMATIC-CONTAINING POLYMERIC DISPERSANTS

CROSS-REFERENCE TO RELATED APPLICATIONS

This application claims the benefit of U.S. Provisional Patent Application No. 61/954,857 filed Mar. 18, 2014, incorporated herein by reference in its entirety, and claims the benefit of U.S. Provisional Patent Application No. 61/954,852 filed Mar. 18, 2014, incorporated herein by reference in its entirety.

FIELD OF THE INVENTION

The present invention relates to novel monomers, polymers and copolymers comprising such monomers, as well as compositions and methods using such polymers in various applications, in particular as polymeric dispersants in coatings applications.

BACKGROUND OF THE INVENTION

Dispersants are widely used in coating industries to disperse inorganic or organic pigments. Dispersants can be divided to small molecules and polymers with varied chemistries. Compared to small molecule dispersants, polymeric dispersants show better dispersing efficiency and stability for many pigments especially inorganic pigments. Most widely used polymeric dispersants are based on acrylic acid homopolymer or copolymers. However, pigment slurries especially aqueous slurries containing such dispersants have very limited shelf life from a couple weeks to months. This is because these dispersants have drawbacks in providing sufficient stabilization, which often times cause the settling of pigment. Therefore, it is still challenging in the coating industry to develop an efficient dispersant to improve the stability of pigment.

SUMMARY OF THE INVENTION

In one aspect, described herein are unsaturated monomers according to structure (D.I):

$$R^{18}-R^{14}-R^{13}-R^{12}-R^{11} \quad (D.I).$$

$R^{12}$ is absent or is a bivalent linking group,
$R^{13}$ is bivalent polyether group,
$R^{14}$ is absent or is a bivalent linking group;
$R^{18}$ is a moiety having a site of ethylenic unsaturation; and
$R^{11}$ is according to structure D.XII

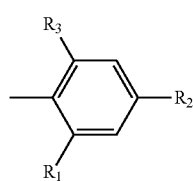

D.XII wherein $R_1$, $R_2$ and $R_3$ are independently selected from H, any of following structures D.XIIa, D.XIIb, D.XIIc, D.XIId:

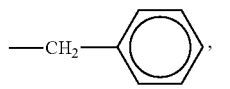

D.XIIIa

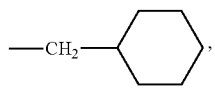

D.XIIIb

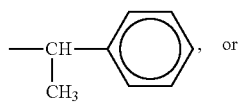

D.XIIIc

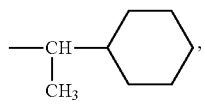

D.XIIId or a $C_2$-$C_{30}$ branched or linear alkyl group or alkenyl group;
wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In another aspect, described herein are unsaturated monomers according to structure (D.I):

$$R^{18}-R^{14}-R^{13}-R^{12}-R^{11} \quad (D.I).$$

$R^{12}$ is absent or is a bivalent linking group,
$R^{13}$ is bivalent polyether group,
$R^{14}$ is absent or is a bivalent linking group;
$R^{18}$ is a moiety having a site of ethylenic unsaturation; and
$R^{11}$ a tri-substituted aromatic group according to the structure D.XII

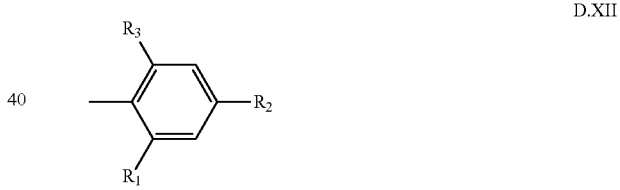

D.XII wherein $R_1$, $R_2$ and $R_3$ are independently selected from the following structures D.XIIa, D.XIIb, D.XIIc, D.XIId:

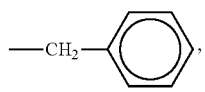

D.XIIIa

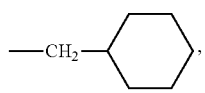

D.XIIIb

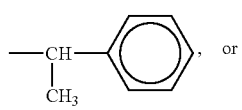

D.XIIIc

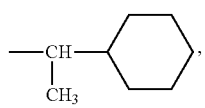

D.XIIId or a $C_2$-$C_{30}$ branched or linear alkyl group or alkenyl group;

wherein at least one of $R_1$, $R_2$ and $R_3$ is the $C_2$-$C_{30}$ branched or linear alkyl group or alkenyl group, and at least one of $R_1$, $R_2$ and $R_3$ is selected from structure D.XIIa, D.XIIb, D.XIIc, or D.XIId.

In one embodiment, $R_{12}$ is —$(CH_2)_xO$—, wherein x is an integer from 1 to 20 (e.g., use of styrenated benzyl alcohols)

In another embodiment, $R_{12}$ is —$CH_2CH(OH)CH_2O$— or —$CH_2CH(CH_2OH)O$— (e.g., use of epichlorohydrin as coupling agent)

In one embodiment, $R_{13}$ is:
—$[CH(R_{20})CH(R_{21})O]_x$— wherein x is an integer of from 0 to 100, and $R_{20}$ and $R_{21}$ are independently selected from any of the following:

H; —$CH_2OH$; phenyl; —$CH_2Cl$;

a $C_1$-$C_{30}$ straight or branched alkyl or alkenyl;

—$CH_2OR_{22}$ wherein $R_{22}$ is $C_1$-$C_{30}$ straight or branched alkyl or alkenyl, phenyl, or alkyl substituted phenyl; or R'COOCH$_2$— where R' is $C_1$-$C_{30}$ straight or branched alkyl or alkenyl.

In another aspect, the invention is directed to polymeric dispersant (co)polymer of a mixture of unsaturated copolymerizable monomers, the unsaturated copolymerizable monomers comprising, based on total weight of monomers:

A. about 0 to 60 weight percent, preferably 5 to 30 weight percent or 10 to 45 weight percent, of at least one $C_3$-$C_8$ alpha beta-ethylenically unsaturated acidic monomer, preferably a $C_3$-$C_8$ alpha beta-ethylenically unsaturated carboxylic acid monomer;

B. about 15 to 70 weight percent, typically 20 to 50 weight percent, of at least one non-ionic, copolymerizable $C_2$-$C_{12}$ alpha, beta-ethylenically unsaturated monomer; and C. about 0.01 to 50 weight percent (wt %), or in another embodiment 0.05 to 30 weight percent, or in another embodiment 0.5 to 10 weight percent, or in another embodiment 1 to 10 weight percent, or in another embodiment 0.5 to 9 weight percent, or in another embodiment 0.5 to 7 weight percent, or in another embodiment 4 to 10 weight percent, of at least one non-ionic ethylenically unsaturated hydrophobic monomer as described herein.

The polymeric dispersant (co)polymer can, in one embodiment, be a homopolymer or, in another embodiment, be a copolymer comprising two or more different monomeric units.

The present invention also includes compositions such as aqueous dispersions comprising this polymeric dispersant (co)polymer. In particular the invention is also directed using the polymeric dispersant copolymer as an additive for latex binders, paints and aqueous coatings, typically as to aid in dispersing generally hydrophobic compounds such as pigments and the like. The aqueous coating compositions as described herein typically include at least one latex polymer derived from at least one monomer, for example acrylic monomers. The at least one latex polymer in the aqueous coating composition can be a pure acrylic, a styrene acrylic, a vinyl acrylic or an acrylated ethylene vinyl acetate copolymer and is more preferably a pure acrylic. The at least one latex polymer is preferably derived from at least one acrylic monomer selected from the group consisting of acrylic acid, acrylic acid esters, methacrylic acid, and methacrylic acid esters. For example, the at least one latex polymer can be a butyl acrylate/methyl methacrylate copolymer or a 2-ethylhexyl acrylate/methyl methacrylate copolymer. Typically, the at least one latex polymer is further derived from one or more monomers selected from the group consisting of styrene, alpha-methyl styrene, vinyl chloride, acrylonitrile, methacrylonitrile, ureido methacrylate, vinyl acetate, vinyl esters of branched tertiary monocarboxylic acids, itaconic acid, crotonic acid, maleic acid, fumaric acid, ethylene, and $C_4$-$C_8$ conjugated dienes.

Latex paint formulations typically comprise additives, e.g., at least one pigment. In a preferred embodiment of the invention the latex paint formulation includes at least one pigment selected from the group consisting of TiO2, CaCO3, clay, aluminum oxide, silicon dioxide, magnesium oxide, sodium oxide, potassium oxide, talc, barytes, zinc oxide, zinc sulfite and mixtures thereof. More preferably the at least one pigment includes TiO2, calcium carbonate or clay.

In addition to the above components, the aqueous coating composition can include one or more additives selected from the group consisting of dispersants, surfactants, rheology modifiers, defoamers, thickeners, biocides, mildewcides, colorants, waxes, perfumes and co-solvents.

Compositions of the present invention may have an absence of one or more of anionic surfactant, cationic surfactant, nonionic surfactant, zwitterionic surfactant, and/or amphoteric surfactant.

In another aspect, described herein are methods for dispersing pigments in an aqueous emulsion, comprising: contacting (i) an aqueous emulsion containing at least one pigment with (ii) the polymeric dispersant copolymer or homopolymer as described herein. In one embodiment, the polymeric dispersant copolymer comprises, based on total weight of monomers:

A. about 0-60 weight percent of the at least one $C_3$-$C_8$ alpha beta-ethylenically unsaturated acidic monomer, preferably a $C_3$-$C_8$ alpha beta-ethylenically unsaturated carboxylic acid monomer;

B. about 15-70 weight percent of the at least one non-ionic, copolymerizable $C_2$-$C_{12}$ alpha, beta-ethylenically unsaturated monomer; and C. about 0.01-30 weight percent of the at least one ethylenically unsaturated hydrophobic monomer according to structure D.XVI:

$$CH_2=\underset{R^{19}}{\overset{\overset{\displaystyle O}{\|}}{C}}-C-O-[(C_gH_{2g}O)_i-(C_hH_{2h}O)_j]_k-(CH_2)_b-R^{11} \quad \text{(D.XVI)}$$

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is a tri-substituted aromatic group according to the structure D.XII

D.XII

[benzene ring with substituents $R_3$, $R_2$, and $R_1$]

wherein $R_1$, $R_2$ and $R_3$ are independently selected from the following structures D.XIIa, D.XIIb, D.XIIc, D.XIId:

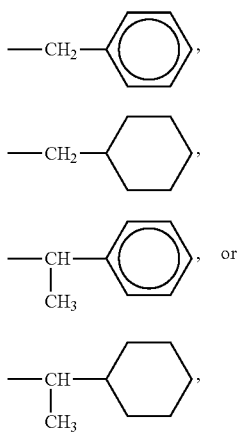

D.XIIIa

D.XIIIb

D.XIIIc

D.XIIId or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId; and wherein the polymeric dispersant has a weight average molecular weight of between 2,000 g/mole to 25,000 g/mole. In one particular embodiment, the pigment is carbon black.

These and other features and advantages of the present invention will become more readily apparent to those skilled in the art upon consideration of the following detailed description, which describe both the preferred and alternative embodiments of the present invention.

BRIEF DESCRIPTION OF THE DRAWINGS

FIG. 1 shows a dispersant demand curve of a polymeric dispersant copolymer of the present invention as compared to a comparative example.

DETAILED DESCRIPTION OF THE PREFERRED EMBODIMENTS

The present invention relates to, in one embodiment, the use of a particular family of polymeric dispersant copolymers for latex dispersions, binders, paints and coatings. Described herein are aqueous compositions, for example, aqueous coating compositions. The aqueous compositions of the invention are aqueous polymer dispersions which include at least one latex polymer. Paints or other aqueous coatings of the present invention typically further include at least one pigment. In another embodiment, the latex has a Tg of less than 30° C., more typically less than 20° C., still more typically in the range from 10 to −10° C., e.g., 0° C. In one embodiment, the latex has a Tg of less than 10° C., more typically less than 5° C., still more typically in the range from 5 to −10° C., e.g., 0° C.

As used herein, the term "alkyl" means a monovalent straight or branched saturated hydrocarbon radical, more typically, a monovalent straight or branched saturated ($C_1$-$C_{40}$) hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tetracontyl.

As used herein, the term "alkenyl" means an unsaturated straight or branched hydrocarbon radical, more typically an unsaturated straight, branched, ($C_2$-$C_{22}$) hydrocarbon radical, that contains one or more carbon-carbon double bonds, such as, for example, ethenyl, n-propenyl, iso-propenyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a ($C_1$-$C_{22}$)alkyloxy-($C_1$-$C_6$)alkyl radical, such as methoxymethyl, and ethoxybutyl.

As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "arylalkyl" means an alkyl group substituted with one or more aryl groups, more typically a ($C_1$-$C_{18}$)alkyl substituted with one or more ($C_6$-$C_{14}$)aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$) alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclic" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a ($C_1$-$C_{22}$)alkyl radical, that is substituted with one or more hydroxyl groups, such as for example, hydroxymethyl, hydroxyethyl, hydroxypropyl, and hydroxydecyl.

As used herein the term "(meth)acrylate" refers collectively and alternatively to the acrylate and methacrylate and the term "(meth)acrylamide" refers collectively and alternatively to the acrylamide and methacrylamide, so that, for example, "butyl (meth)acrylate" means butyl acrylate and/or butyl methacrylate.

As used herein, "molecular weight" in reference to a polymer or any portion thereof, means to the weight-average molecular weight ("$M_w$") of the polymer or portion. $M_w$ of a polymer is a value measured by gel permeation chromatography (GPC) with an aqueous eluent or an organic eluent (for example dimethylacetamide, dimethylformamide, and the like), depending on the composition of the polymer, light scattering (DLS or alternatively MALLS), viscometry, or a number of other standard techniques. $M_w$ of a portion of a polymer is a value calculated according to known techniques from the amounts of monomers, polymers, initiators and/or transfer agents used to make the portion.

In one embodiment, the copolymers for use in the present invention exhibit a weight average molecular weight, as determined by gel permeation chromatography (GPC) and light scattering of a solution of the polymer in tetrahydrofuran and compared to a polystyrene standard, of between 2,000 to 29,000 grams per mole ("g/mole"). In another embodiment, the copolymers for use in the present invention exhibit a weight average molecular weight 2,000 to 25,000 grams per mole ("g/mole"). In yet another embodiment, the copolymers for use in the present invention exhibit a weight average molecular weight 2,000 to 15,000 grams per mole ("g/mole"). In yet another embodiment, the copolymers for use in the present invention exhibit a weight average molecular weight 2,000 to 100,000 grams per mole ("g/mole"). In yet another embodiment, the copolymers for use in the present invention exhibit a weight average molecular weight 2,000 to 50,000 grams per mole ("g/mole"). In yet another embodiment, the copolymers for use in the present invention exhibit a weight average molecular weight 2,000 to 75,000 grams per mole ("g/mole").

As used herein, the indication that a radical may be "optionally substituted" or "optionally further substituted" means, in general, unless further limited either explicitly or by the context of such reference, such radical may be substituted with one or more inorganic or organic substituent groups, for example, alkyl, alkenyl, aryl, arylalkyl, alkaryl, a hetero atom, or heterocyclyl, or with one or more functional groups capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as MIRATAINE BET C-30)" means 10 pbw of the actual betaine compound, added in the form of a commercially available aqueous solution of the betaine compound having the trade name "MIRATAINE BET C-30", and exclusive of the water contained in the aqueous solution.

As used herein, an indication that a composition is "substantially free" of a specific material, means the composition contains no more than an insubstantial amount of that material, and an "insubstantial amount" means an amount that does not measurably affect the desired properties of the composition.

As used herein, the term "surfactant" means a compound that reduces surface tension when dissolved in water.

"Surfactant effective amount" means the amount of the surfactant that provides a surfactant effect to enhance the stability of emulsions of the polymers.

In one embodiment, described herein are polymeric dispersant copolymers of a mixture of unsaturated copolymerizable monomers.

In one embodiment, the copolymer comprises a chain of monomeric units. The polymer is an oligomer having a relatively low molecular mass that comprises chains of multiple repetitions of the monomeric units, which are derived, actually or conceptually, from molecules of relatively low molecular mass and are connected to form a linear, branched, or network structure. The polymeric dispersant copolymer typically has a linear or branched structure, more typically single strand linear or branched structure. In one embodiment, a polymer having a predominantly single strand linear or branched structure is lightly cross-linked to form a polymer network having a low density of crosslinks. As used herein the term "single strand" in regard to a polymer means monomeric units of the polymer are connected such that adjacent monomeric units are joined to each other through two atoms, one on each of the adjacent monomeric units.

The copolymer may typically be regarded as having a "backbone", or main polymer chain, from which all branches and substituent groups of the polymer may be regarded as being pendant. Where two or more chains of the copolymer could equally be considered to be the main chain of the polymer, that chain is selected as the main chain which leads to the simplest representation of the polymer molecule. The monomeric units of the copolymer may be arranged in random, alternating, tapered, or block sequence along the copolymer chain.

The polymer of the present invention, in one embodiment, further comprises one or more acidic monomeric units, each independently comprising at least one acid group per acidic monomeric unit.

In one embodiment, the acidic monomeric units each independently comprise, per monomeric unit, at least one group according to structure (B.I):

$$-R^{32}-R^{31} \qquad (B.I)$$

wherein
$R^{31}$ is a moiety that comprises at least one carboxylic acid, sulfonic acid, or phosphoric acid group, and
$R^{32}$ is absent or is a bivalent linking group.

In one embodiment, $R^{32}$ is O, —(CH$_2$)$_n$—O—, or is according to structure (structure (B.II):

(B.II)

wherein:

n is an integer of from 1 to 6,

A is O or $NR^{17}$, and $R^{17}$ is H or $(C_1\text{-}C_4)$alkyl.

In one embodiment, the one or more acidic monomeric units each independently comprise one or two carboxy groups per monomeric unit and may, if the acidic monomeric unit comprises a single carboxy group, further comprise an ester group according to $-CH_2COOR^{33}$, wherein $R^{33}$ is alkyl, more typically, $(C_1\text{-}C_6)$alkyl.

The acidic monomeric units may be made by known synthetic techniques, such as, for example, by grafting of one or more groups according to structure (B.I) onto a polymer backbone, such as a hydrocarbon polymer backbone, a polyester polymer backbone, or a polysaccharide polymer backbone. In the alternative, they may be made by polymerizing a monomer that comprises a reactive functional group and at least one group according to structure (B.I) per molecule.

In one embodiment the acidic monomer comprises one or more ethylenically unsaturated monocarboxylic acid monomers according to structure (B.III):

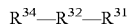  (B.III)

wherein:

$R^{31}$ and $R^{32}$ are each as described above, and $R^{34}$ is a moiety having a site of ethylenic unsaturation.

In one embodiment, $R^{34}$ is a α-, β-unsaturated carbonyl compound. In one embodiment, $R^{34}$ is according to structure (B.IV):

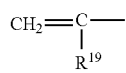  (B.IV)

wherein $R^{19}$ is H or $(C_1\text{-}C_4)$alkyl.

Suitable acidic monomers include, for example, ethylenically unsaturated carboxylic acid monomers, such as acrylic acid and methacrylic acid, ethylenically unsaturated dicarboxylic acid monomers, such as maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups. The preferred acidic monomeric units are derived from one or more monomers selected from acrylic acid, methacrylic acid, and mixtures thereof. Methacrylic acid has the following formula B. V:

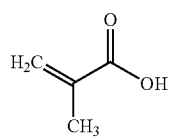  B.V.

In one embodiment, the polymer of the present invention further comprises one or more nonionic monomeric units.

In one embodiment, the nonionic monomeric units each independently comprise, per monomeric unit, at least one group according to structure (C.I):

$-R^{42}-R^{41}$   (C.I)

wherein $R^{41}$ is alkyl, hydroxyalkyl, alkoxyalkyl, cycloalkyl, aryl, arylalkyl, or aryloxy, and $R^{42}$ is absent or is a bivalent linking group.

In one embodiment, $R^{41}$ is $(C_1\text{-}C_{22})$alkyl, $(C_1\text{-}C_{22})$hydroxyalkyl, $(C_2\text{-}C_{22})$alkoxyalkyl, $(C_6\text{-}C_{24})$cycloalkyl, $(C_6\text{-}C_{40})$aryl, or $(C_7\text{-}C_{40})$arylalkyl, more typically $(C_2\text{-}C_{12})$alkyl.

In one embodiment, $R^{41}$ is $(C_1\text{-}C_{22})$alkyl, more typically, $(C_1\text{-}C_{12})$alkyl.

In one embodiment, $R^{42}$ is O, $-(CH_2)_n-O-$, wherein n is an integer of from 1 to 6, or is according to structure (C.II):

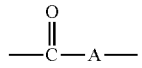  (C.II)

wherein:

n is an integer of from 1 to 6,

A is O or $NR^{17}$, and $R^{17}$ is H or $(C_1\text{-}C_4)$alkyl.

The nonionic monomeric units may be made by known synthetic techniques, such as, for example, by grafting of one or more groups onto a polymer backbone, such as a hydrocarbon polymer backbone, a polyester polymer backbone, or a polysaccharide polymer backbone, or a backbone made by polymerization, with, for example, the above described acidic, and hydrophobic monomers and copolymerizable with the first, second, and third monomers. Alternatively, the nonionic monomeric units may simply be non-grafted portions of a polymer backbone.

In one embodiment, the nonionic monomeric units are derived from a nonionic monomer, for example, ethyl acrylate, that comprises a reactive functional group, and is copolymerizable with the acidic monomers and hydrophobic monomers as described herein.

In one embodiment, the reactive functional group of the nonionic monomer is an ethylenically unsaturated group and the nonionic monomer is an ethylenically unsaturated monomer comprising at least one site of ethylenic unsaturation, more typically, an α-, β-unsaturated carbonyl moiety and at least one other group.

In one embodiment, the nonionic monomer comprises one or more compounds according to structure (C.III):

$R^{43}-R^{42}-R^{41}$   (C.III)

wherein:

$R^{41}$ and $R^{42}$ are each as described above, and $R^{43}$ is a moiety having a site of ethylenic unsaturation.

In one embodiment, the compound according to structure (C.III) is an α-, β-unsaturated carbonyl compound. In one embodiment, $R^{43}$ is according to structure (C.IV):

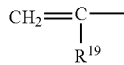  (C.IV)

wherein $R^{19}$ is H or $(C_1\text{-}C_4)$alkyl.

Suitable nonionic monomers include unsaturated monomers include (meth)acrylic esters such as: methyl (meth)acrylate, ethyl (meth)acrylate, butyl (meth)acrylate, isobutyl (meth)acrylate, cyclohexyl(meth)acrylate, 2-ethylhexyl (meth)acrylate, isodecyl(meth)acrylate, lauryl(meth)acrylate isobornyl(meth)acrylate, benzyl (meth)acrylate, hydroxyethyl(meth)acrylate, hydroxypropyl(meth)acrylate, methoxyethyl(meth)acrylate, ethoxyethyl(meth)acrylate, phenoxyethyl(meth)acrylate, tetrahydrofurfuryl(meth)acrylate, glycidyl(meth)acrylate, dimethylaminoethyl(meth)acrylate, diethylaminoethyl(meth)acrylate, tert-butylaminoethyl(meth)acrylate, and acetoxyethyl(meth)acrylate, (meth)acrylamides such as, (meth)acrylamide, N-methylol(meth)acrylamide, N-butoxyethyl(meth)acrylamide, N,N-dimethyl (meth)acrylamide, N-isopropyl(meth)acrylamide, N-tert-butyl (meth)acrylamide, N-tert-octyl(meth)acrylamide, and diacetone(meth)acrylamide, vinyl esters such as vinyl acetate, vinyl propionate, vinyl 2-ethylhexanoate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the polymeric dispersant copolymer of the present invention is crosslinked. A crosslinked polymer can be made by, for example, reacting a mixture of hydrophobic, first acidic, and second acidic monomers with a nonionic monomer having more than one reactive functional group, such as for example, more than one site of ethylenic unsaturation per molecule. In one embodiment, the nonionic monomer comprises least one monomeric compound having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof.

Ethylene glycol dimethyl acrylate having the following formula

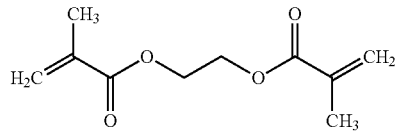

The polymeric dispersant copolymer is made from a mixture of unsaturated copolymerizable monomers, wherein at least one is a novel monomer comprising, based on total weight of monomers:

A. about 0.1-70 weight percent, typically 0.5-50, 0.7-40, 1-40, 5-40, 5-30 or 10 to 40 weight percent, of at least one alpha beta-ethylenically unsaturated monomer according to structure D.XVI. In one embodiment, the novel monomer according to the present invention comprises, based on total weight of monomers: about 0.01 to 50 weight percent (wt %), or in another embodiment 0.05 to 30 weight percent, or in another embodiment 0.5 to 10 weight percent, or in another embodiment 1 to 10 weight percent, or in another embodiment 0.5 to 9 weight percent, or in another embodiment 0.5 to 7 weight percent, or in another embodiment 4 to 10 weight percent.

In one embodiment, the unsaturated monomer is an ethylenically unsaturated hydrophobic monomer comprising a compound according to structure D.XVI:

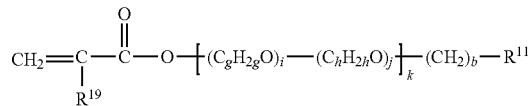

(D.XVI)

wherein:
g is an integer from 2 to 4;
h is an integer from 2 to 4;
b is an integer from 0 to 1;
k is an integer from 0 to 100, or from 0 to 25;
i is an integer from 0 to 40, or from 0 to 20;
j is an integer from 0 to 40, or from 0 to 20;
R19 is hydrogen; methyl or ethyl;
$R^{11}$ is a tri-substituted aromatic group according to the structure D.XII

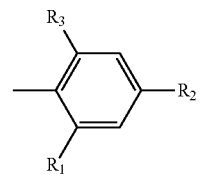

D.XII wherein $R_1$, $R_2$ and $R_3$ are independently selected from the following structures D.XIIa, D.XIIb, D.XIIc, D.XIId:

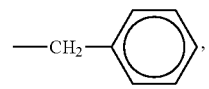

D.XIIIa

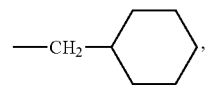

D.XIIIb

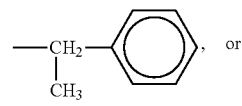, or

D.XIIIc

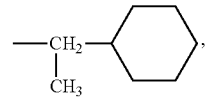

D.XIIId or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

In one embodiment, the $C_2$-$C_{30}$ branched or linear alkyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group. In one embodiment, the $C_2$-$C_{30}$ branched or linear alkyl group is a $C_9$-$C_{14}$ branched or linear alkyl group or alkenyl group. In one embodiment, the $C_2$-$C_{30}$ branched or linear alkyl group is a $C_8$-$C_{12}$ branched or linear alkyl group or alkenyl group. In one embodiment, the $C_2$-$C_{30}$ branched or linear alkyl group is a $C_{23}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In another embodiment, at least one of $R_1$, $R_2$ and $R_3$ is a branched or linear alkyl group or alkenyl group having, as a lower limit, a $C_2$ linear alkyl group, or in another embodiment, a $C_3$ branched or linear alkyl group or alkenyl group, or in another embodiment, a $C_4$ branched or linear alkyl group or alkenyl group, or in a further embodiment, a $C_5$ branched or linear alkyl group or alkenyl group, or in another embodiment, a $C_6$ branched or linear alkyl group or alkenyl group, or in yet another embodiment, a $C_7$ branched or linear alkyl group or alkenyl group, or in another embodiment, a $C_8$ branched or linear alkyl group or alkenyl group, or in another embodiment, a $C_9$ branched or linear alkyl group or alkenyl group, or in another embodiment, a $C_{10}$ branched or linear alkyl group or alkenyl group, or in another embodiment, a $C_{12}$ branched or linear alkyl group or alkenyl group, or in another embodiment, a $C_{14}$ branched or linear alkyl group or alkenyl group, or in yet a further embodiment, a $C_{16}$ branched or linear alkyl group or alkenyl group.

In one embodiment, the unsaturated monomer is an ethylenically unsaturated hydrophobic monomer comprising a compound according to structure D.XXX:

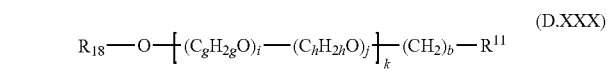

wherein:
g is an integer from 2 to 4;
h is an integer from 2 to 4;
b is an integer from 0 to 1;
k is an integer from 0 to 100;
i is an integer from 0 to 40, or from 0 to 20;
j is an integer from 0 to 40, or from 0 to 20;
$R^{18}$ is a moiety having a site of ethylenic unsaturation;
$R^{11}$ is a tri-substituted aromatic group according to the structure D.XII

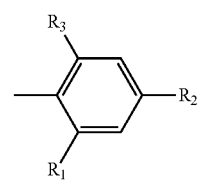

wherein $R_1$, $R_2$ and $R_3$ are independently selected from the following structures D.XIIa, D.XIIb, D.XIIc, D.XIId:

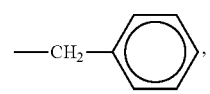

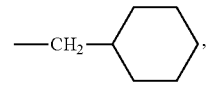

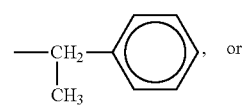

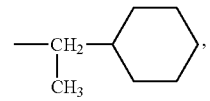

or a $C_2$-$C_{30}$ branched or linear alkyl group or alkenyl group; wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIa, D.XIIb, D.XIIc, or D.XIId.

In one embodiment, $R^{18}$ is according to structure (D.XV):

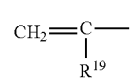

wherein $R^{19}$ is H or $(C_1$-$C_4)$alkyl.

The $C_2$-$C_{30}$ branched or linear alkyl group or alkenyl group can be a $C_3$-$C_{14}$ branched or linear alkyl group or alkenyl group, or a $C_6$-$C_{14}$ branched or linear alkyl group or alkenyl group, or a $C_8$-$C_{12}$ branched or linear alkyl group or alkenyl group, or a $C_4$-$C_{12}$ branched or linear alkyl group or alkenyl group. Preferably, The $C_2$-$C_{30}$ branched or linear alkyl group or alkenyl group can be a $C_8$-$C_{12}$ branched or linear alkyl group or alkenyl group, or a $C_4$-$C_{12}$ branched or linear alkyl group or alkenyl group.

In one embodiment, the $C_2$-$C_{30}$ branched or linear alkyl group or alkenyl group is a $C_3$-$C_{30}$ branched or linear alkyl group or alkenyl group. In one embodiment, the $C_2$-$C_{30}$ branched or linear alkyl group or alkenyl group is a $C_4$-$C_{30}$ branched or linear alkyl group or alkenyl group. In one embodiment, the $C_2$-$C_{30}$ branched or linear alkyl group or alkenyl group is a $C_5$-$C_{30}$ branched or linear alkyl group or alkenyl group. In one embodiment, the $C_2$-$C_{30}$ branched or linear alkyl group or alkenyl group is a $C_6$-$C_{30}$ branched or linear alkyl group or alkenyl group. In one embodiment, the $C_2$-$C_{30}$ branched or linear alkyl group or alkenyl group is a $C_7$-$C_{30}$ branched or linear alkyl group or alkenyl group. In one embodiment, the $C_2$-$C_{30}$ branched or linear alkyl group or alkenyl group is a $C_8$-$C_{30}$ branched or linear alkyl group or alkenyl group. In one embodiment, the $C_2$-$C_{30}$ branched or linear alkyl group or alkenyl group is a $C_9$-$C_{30}$ branched or linear alkyl group or alkenyl group. In one embodiment, the $C_2$-$C_{30}$ branched or linear alkyl group or alkenyl group is a $C_{10}$-$C_{30}$ branched or linear alkyl group or alkenyl group.

In another embodiment, the $C_2$-$C_{30}$ branched or linear alkyl group or alkenyl group is a $C_2$-$C_{28}$ branched or linear alkyl group or alkenyl group. In one embodiment, the $C_2$-$C_{30}$ branched or linear alkyl group or alkenyl group is a $C_3$-$C_{26}$ branched or linear alkyl group or alkenyl group. In one embodiment, the $C_2$-$C_{30}$ branched or linear alkyl group or alkenyl group is a $C_4$-$C_{24}$ branched or linear alkyl group or alkenyl group. In one embodiment, the $C_2$-$C_{30}$ branched or linear alkyl group or alkenyl group is a $C_6$-$C_{24}$ branched or linear alkyl group or alkenyl group. In another embodiment, the $C_8$-$C_{24}$ branched or linear alkyl group or alkenyl group is a $C_{10}$-$C_{24}$ branched or linear alkyl group or alkenyl group.

In another embodiment, the $C_2$-$C_{30}$ branched or linear alkyl group or alkenyl group is a $C_6$-$C_{20}$ branched or linear alkyl group or alkenyl group. In another embodiment, the $C_2$-$C_{30}$ branched or linear alkyl group or alkenyl group is a $C_6$-$C_{18}$ branched or linear alkyl group or alkenyl group. In another embodiment, the $C_2$-$C_{30}$ branched or linear alkyl group or alkenyl group is a $C_8$-$C_{16}$ branched or linear alkyl group or alkenyl group.

In one embodiment, the $R^{11}$ is a tri-substituted aromatic group according to the structure D.XII

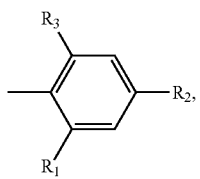

D.XII wherein $R_1$, $R_2$ and $R_3$ are independently selected from:
a styryl group, or
a $C_2$-$C_{30}$ branched or linear alkyl group or alkenyl group;
wherein at least one of $R_1$, $R_2$ and $R_3$ is the $C_2$-$C_{30}$ branched or linear alkyl group or alkenyl group and at least one of $R_1$, $R_2$ and $R_3$ is the styryl group.

In another embodiment, the $R^{11}$ is a tri-substituted aromatic group is according to structure D.XII-1:

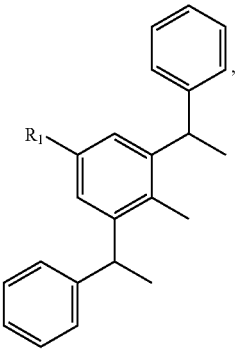

D.XII-1 wherein $R_1$, is the $C_2$-$O_{30}$ branched or linear alkyl group or alkenyl group The copolymers can further comprise hydrophobic monomeric units derived from a hydrophobic monomer. These hydrophobic monomers are ethylenically unsaturated hydrophobic monomers.

In one embodiment, the hydrophobic monomeric units each independently comprise a tri-substituted group according to structure (D.I):

$$—R^{14}—R^{13}—R^{12}—R^{11} \qquad (D.I).$$

$R^{12}$ is absent or is a bivalent linking group,
$R^{13}$ is bivalent polyether group, and
$R^{14}$ is absent or is a bivalent linking group.
$R^{11}$ is according to structure (D.XII), above;
More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (D.VIII):

$$—(CH_2)_b-A- \qquad (D.IX)$$

wherein A is O or absent, and b is an integer of from 1 to 6.
More typically, $R^{13}$ is a bivalent polyether group comprising a linear chain of from 2 to 100 units, each of which may independently be $(C_2$-$C_4)$oxyalkylene, more typically, $(C_2$-$C_3)$oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R_{12}$ is —$(CH_2)_xO$—, wherein x is an integer from 1 to 20 (e.g., use of styrenated benzyl alcohols)
In another embodiment, $R_{12}$ is —$CH_2CH(OH)CH_2O$— or —$CH_2CH(CH_2OH)O$— (e.g., use of epichlorohydrin as coupling agent)
In one embodiment, $R_{13}$ is:
—$[CH(R_{20})CH(R_{21})O]_x$— wherein x is an integer of from 0 to 100, and $R_{20}$ and $R_{21}$ are independently selected from any of the following:
H; —$CH_2OH$; phenyl; —$CH_2Cl$;
a $C_1$-$C_{30}$ straight or branched alkyl or alkenyl;
—$CH_2OR_{22}$ wherein $R_{22}$ is $C_1$-$C_{30}$ straight or branched alkyl or alkenyl, phenyl, or alkyl substituted phenyl; or R'COOCH$_2$— where R' is C$_1$-C$_{30}$ straight or branched alkyl or alkenyl.

In one embodiment, R$^{13}$ is according to structure (D.X):

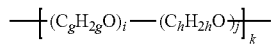
(D.X)

wherein:

g and h are independently integers of from 2 to 5, more typically 2 or 3, each i is independently an integer of from 1 to about 80, more typically from 1 to about 50, each j is independently an integer of from 0 to about 80, more typically from 1 to about 50, k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

If i≠0, j≠0, and g≠h, the respective —(C$_p$H$_{2p}$O)— and (—(C$_q$H$_{2q}$O)— oxylakylene units may be arranged randomly, in blocks, or in alternating order.

In one embodiment, g=2, h=3, i is an integer of from 1 to 50, more typically 10 to 40, and even more typically from 15 to about 30, j is an integer of from 1 to 30, more typically from 2 to 20, and even more typically from about 2 to about 10, and k=1.

In one embodiment, R$^{14}$ is O, —(CH$_2$)$_n$—O—, or is according to structure (D.XI):

(D.XI)

wherein:

n is an integer of from 1 to 6,

A is O or NR$^{17}$, and

R$^{17}$ is H or (C$_1$-C$_4$)alkyl.

In another embodiment of structure (D.I) R$^1$ is a trisubstituted group according to the following structure D.XII.

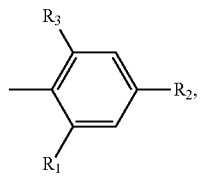
(D.XII)

wherein R$_1$, R$_2$ and R$_3$ are independently selected from the following structures:

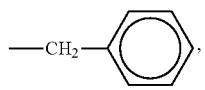
(D.XIIIa)

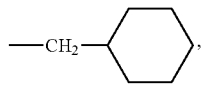
(D.XIIIb)

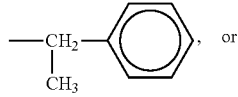
(D.XIIIc)

or

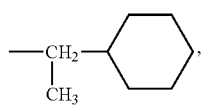
(D.XIIId)

or a C$_2$-C$_{30}$ branched or linear alkyl group or alkenyl group.

In one embodiment, at least one of R$_1$, R$_2$ and R$_3$ is the C$_2$-C$_{30}$ branched or linear alkyl group or alkenyl group and at least one of R$_1$, R$_2$ and R$_3$ is selected from structure D.XIIa, D.XIIb, D.XIIc, or D.XIId.

The hydrophobic monomeric units may be made by known synthetic techniques, such as, for example, by grafting of one or more groups according to structure (D.I) onto a polymer backbone, such as a hydrocarbon polymer backbone, a polyester polymer backbone, or a polysaccharide polymer backbone, or by copolymerization, with, for example, the acidic monomer and nonionic monomer described above, of at least one other monomer selected from monomers that comprise a reactive functional group and at least one group according to structure (D.I) per molecule.

In one embodiment, the hydrophobic monomeric units are derived from at least one hydrophobic monomer selected from monomers that comprise a reactive functional group and at least one group according to structure (D.I) per molecule.

In one embodiment, the reactive functional group of the first monomer is an ethylenically unsaturated group. Thus, the hydrophobic monomer is selected from ethylenically unsaturated monomers that comprise at least one site of ethylenic unsaturation, more typically, an α-, β-unsaturated carbonyl moiety, and least one group according to structure (I) per molecule.

In one embodiment, the hydrophobic monomer comprises one or more compounds according to structure (D.XIV):

(D.XIV)

wherein:

R$^{11}$, R$^{12}$, R$^{13}$, and R$^{14}$ are each as described above, and R$^{18}$ is a moiety having a site of ethylenic unsaturation.

In one embodiment, the compound according to structure (D.XI) is an α-, β-unsaturated carbonyl compound.

In one embodiment, $R^{18}$ is according to structure (D.XV):

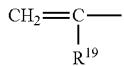

(D.XV)

wherein $R^{19}$ is H or $(C_1-C_4)$alkyl.

In one embodiment, the hydrophobic monomer is selected from monomers according to structure (D.XVI):

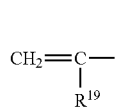

(D.XVI)

wherein:

$R^{11}$ is a tri-substituted group according to the above-discussed structure D.XII.

and $R^{19}$, b, g, h, i, j, and k are each as defined above, namely:

$R^{19}$ is H or $(C_1-C_4)$alkyl, b is an integer of from 1 to 6, g and h are independently integers of from 2 to 5, more typically 2 or 3, each i is independently an integer of from 1 to about 80, more typically from 1 to about 50, each j is independently an integer of from 0 to about 80, more typically from 1 to about 50, k is an integer of from 1 to about 50, provided that the product obtained by multiplying the integer k times the sum of i+j is from 2 to about 100.

In another embodiment k is an integer having a lower limit of 0. In another embodiment k is an integer having a lower limit of 1. In another embodiment k is an integer having a lower limit of 3. In another embodiment k is an integer having a lower limit of 5. In another embodiment k is an integer having a lower limit of 8. In another embodiment k is an integer having a lower limit of 10. In another embodiment k is an integer having an upper limit of 100. In another embodiment k is an integer having an upper limit of 75. In another embodiment k is an integer having an upper limit of 50. In another embodiment k is an integer having an upper limit of 40. In another embodiment k is an integer having an upper limit of 60. In another embodiment k is an integer having an upper limit of 25. In another embodiment k is an integer having an upper limit of 35.

In another embodiment of monomers according to structure (D.XVI) $R^{11}$ is a tri-substituted group according to the following structure D.XII and $R^{19}$, b, g, h, i, j, and k are each as defined above. An example of a suitable monomer has structure D.XVia:

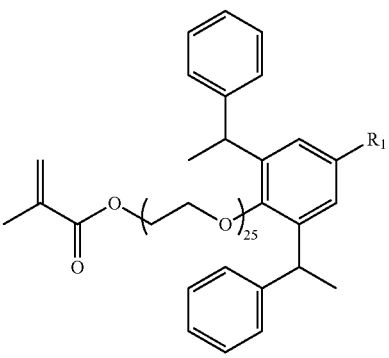

D.XVIa

Wherein $R_1$, $R_2$ and $R_3$ is a $C_2-C_{30}$ branched or linear alkyl group or alkenyl group, typically a $C_4-C_{12}$ branched or linear alkyl group or alkenyl group or a $C_8-C_{12}$ branched or linear alkyl group or alkenyl group.

The hydrophobic monomeric units may be made by known synthetic techniques, for example, by grafting of one or more groups according to structure D.XVII onto a polymer backbone, such as a hydrocarbon polymer backbone, a polyester polymer backbone, or a polysaccharide polymer backbone, or by copolymerization, with, for example, the above-described acidic monomer and the nonionic monomer described above.

In one embodiment, the hydrophobic monomeric units are derived from copolymerizing at least one monomer that comprises a reactive functional group and at least one group according to structure (D.XXI) per molecule.

In one embodiment, the reactive group of the hydrophobic monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (D.XXI) per molecule and copolymerizable with the first monomer.

In one embodiment wherein the nonionic ethylenically unsaturated hydrophobic monomer comprises a compound according to: structure D.XXVIIa, structure D.XXVIIb, structure D.XXVIIc or structure D.XXVIId

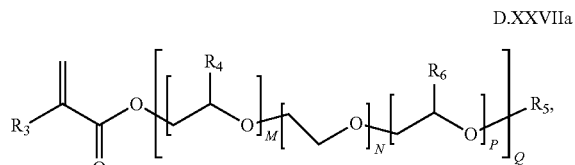

D.XXVIIa

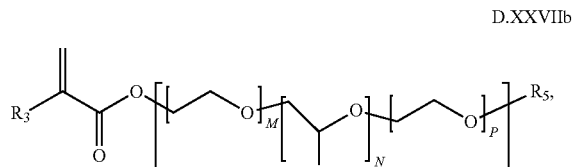

D.XXVIIb

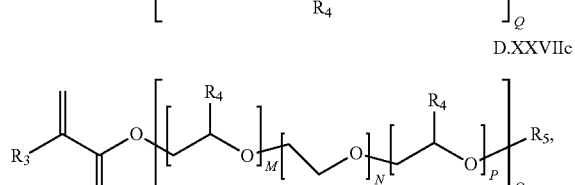

D.XXVIIc

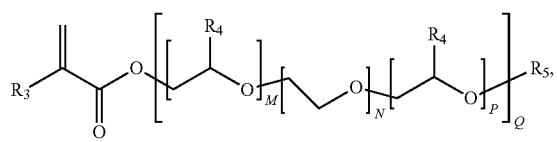

-continued

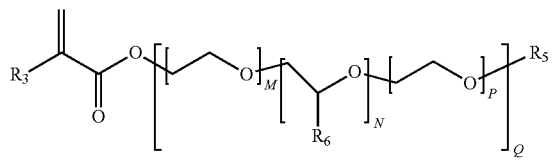
D.XXVIId wherein $R_3$ is H or $CH_3$; $R_4$ is independently an alkyl chain containing 1 to about 4 carbon atoms; $R_6$ is an alkyl chain containing 1 to about 4 carbon atoms; M is an integer from 0 to about 50 (preferably about 1 to 50, more preferably about 5 to 30); N is an integer from 0 to 20 (preferably 1 to 20, more preferably 5 to 15); P is an integer from 0 to about 50 (preferably 0 to 30); wherein P+M is greater than or equal to 1; wherein Q is an integer from 1 to 4 (typically 1 to 2). $R_5$ is a tri-substituted group according to the following structure D.XII.

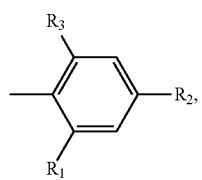
D.XII wherein $R_1$, $R_2$ and $R_3$ are independently selected from the following structures:

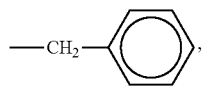
D.XIIIa

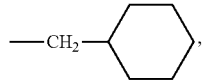
D.XIIIb

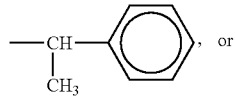
D.XIIIc

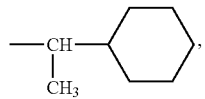
D.XIIId or a $C_2$-$C_{30}$ branched or linear alkyl group or alkenyl group.

In one embodiment, at least one of $R_1$, $R_2$ and $R_3$ is the $C_2$-$C_{30}$ branched or linear alkyl group and at least one of $R_1$, $R_2$ and $R_3$ is selected from structure D.XIIa, D.XIIb, D.XIIc, or D.XIId.

In one embodiment, the polymeric dispersant copolymer is the product of copolymerization of a mixture of monomers, comprising:

A. about 0-60 weight percent, preferably 5 to 30 weight percent, of at least one C3-C8 alpha beta-ethylenically unsaturated acidic monomer, preferably a C3-C8 alpha beta-ethylenically unsaturated carboxylic acid monomer;

B. about 15-70 weight percent, typically 20 to 50 weight percent, of at least one non-ionic, copolymerizable C2-C12 alpha, beta-ethylenically unsaturated monomer.

C. about 0.01 to 30 weight percent, preferably 0.05 to 30 weight percent or typically 5 to 20 weight percent, of at least one non-ionic ethylenically unsaturated hydrophobic monomer.

The polymeric dispersant copolymer of the present invention can be conveniently prepared from the above-described monomers by known aqueous emulsion polymerization techniques using free-radical producing initiators, typically in an amount from 0.01 percent to 3 percent, based on the weight of the monomers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical producing initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature between about 60° C. and 90° C., but higher or lower temperatures may be used. The polymerization can be conducted batchwise, stepwise, or continuously with batch and/or continuous addition of the monomers, in a conventional manner.

The monomers can be copolymerized in such proportions, and the resulting emulsion polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. One or more fourth monomers may be added to adjust the properties of the polymer.

These polymeric products prepared by emulsion polymerization at an acid pH are in the form of stable aqueous colloidal dispersions containing the polymer dispersed as discrete particles having average particle diameters of about 400 to about 3000 Å (40 to 300 nanometers) and preferably about 600 to about 1750 Å (60 to 175 nanometers), as measured by light scattering. Dispersions containing polymer particles smaller than about 400 Å (40 nanometers) are difficult to stabilize, while particles larger than about 3000 Å (300 nanometers) reduce the ease of dispersion in the aqueous products to be thickened.

In one embodiment, the polymer composition is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively this (co)polymerization may also be conducted by different methods or in different solvents. The scope of methods and solvents is well known to those skilled in the art.

Thus, these polymers for use in the present invention can be made using known solution polymerization techniques, wherein the reactant monomers and initiator are dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The polymer product can be isolated through normal separation techniques, including solvent stripping.

In one embodiment, the polymeric dispersant polymers (copolymer or homopolymer) for use in the present invention exhibit a weight average molecular weight, as determined by gel permeation chromatography and light scattering of a solution of the polymer in tetrahydrofuran and compared to a polystyrene standard, of less than 30,000 grams per mole ("g/mole"). In another embodiment, the polymeric dispersant polymers for use in the present invention exhibit a weight average molecular weight of less than 25,000 g/mole. In another embodiment, the polymeric dispersant polymers for use in the present invention exhibit a weight average molecular weight of less than 20,000 g/mole. In another embodiment, the polymeric dispersant polymers for use in the present invention exhibit a weight average molecular weight of less than 15,000 g/mole. In another embodiment, the polymeric dispersant polymers for use in the present invention exhibit a weight average molecular weight of less than 10,000 g/mole.

In another embodiment, the polymeric dispersant polymers for use in the present invention exhibit a weight average molecular weight of less than 100,000 g/mole. In another embodiment, the polymeric dispersant polymers for use in the present invention exhibit a weight average molecular weight of less than 75,000 g/mole. In another embodiment, the polymeric dispersant polymers for use in the present invention exhibit a weight average molecular weight of less than 50,000 g/mole.

In one embodiment, the polymeric dispersant polymers (copolymer or homopolymer) for use in the present invention exhibit a weight average molecular weight, as determined by gel permeation chromatography and light scattering of a solution of the polymer in tetrahydrofuran and compared to a polystyrene standard, of between about 2,000 g/mole and 30,000 g/mole. In another embodiment, the polymeric dispersant polymers for use in the present invention exhibit a weight average molecular weight of between about 2,000 g/mole and 25,000 g/mole. In another embodiment, the polymeric dispersant polymers for use in the present invention exhibit a weight average molecular weight of between about 2,000 g/mole and 20,000 g/mole. In another embodiment, the polymeric dispersant polymers for use in the present invention exhibit a weight average molecular weight of between about 2,000 g/mole and 15,000 g/mole. In another embodiment, the polymeric dispersant polymers for use in the present invention exhibit a weight average molecular weight of between about 2,000 g/mole and 10,000 g/mole.

In one embodiment, these polymeric dispersant copolymers for use in the present invention are in the form of an aqueous colloidal polymer dispersion.

The polymers and polymer compositions according to the present invention are useful as dispersants for a wide variety of applications ranging from coatings, to home care, personal care and oilfield drilling fluids. They are particularly useful for aqueous paints and coatings, wherein the polymeric dispersant copolymer as described herein aids in dispersing generally hydrophobic compounds into an aqueous coatings composition. Such compositions include brine, slurries, and colloidal dispersions of water-insoluble inorganic and organic materials, such as natural rubber, synthetic or artificial latexes.

Synthetic latexes take the form of aqueous dispersions/ suspensions of particles of latex polymers. Synthetic latexes include aqueous colloidal dispersions of water-insoluble polymers prepared by emulsion polymerization of one or more ethylenically unsaturated monomers. Typical of such synthetic latexes are emulsion copolymers of monoethylenically unsaturated compounds, such as styrene, methyl methacrylate, acrylonitrile with a conjugated diolefin, such as butadiene or isoprene; copolymers of styrene, acrylic and methacrylic esters, copolymers of vinyl halide, vinylidene halide, vinyl acetate and the like. Many other ethylenically unsaturated monomers or combinations thereof can be emulsion polymerized to form synthetic latexes. Such latexes are commonly employed in paints (latex paints) and coatings. The composition of the present invention may be added to latexes to modify/increase viscosity.

The polymeric dispersants of this invention are advantageous for use with the water-based compositions according to the foregoing description and with compositions containing those materials, especially coating compositions of various types. Mixtures or combinations of two or more thickeners may be used, if desired. Of course the latex polymers used in coating compositions are preferably film-forming at temperatures about 25 degrees C. or less, either inherently or through the use of plasticizers. Such coating compositions include water-based consumer and industrial paints; sizing, adhesives and other coatings for paper, paperboard, textiles; and the like.

Latex paints and coatings may contain various adjuvants, such as pigments, fillers and extenders. Useful pigments include, but are not limited to, titanium dioxide, mica, iron oxides, carbon black, etc. Useful fillers and extenders include, but are not limited to, barium sulfate, calcium carbonate, clays, talc, and silica The polymer compositions of the present invention may be added to aqueous product systems at a wide range of amounts depending on the desired system properties and end use applications.

The present invention also includes a method of preparing an aqueous coating composition by mixing together at least one latex polymer blended with at least one polymeric dispersant copolymer as described above, and at least one pigment. Preferably, the latex polymer is in the form of latex polymer dispersion. The additives discussed above can be added in any suitable order to the latex polymer, the pigment, or combinations thereof, to provide these additives in the aqueous coating composition.

In formulating latexes and latex paints/coatings, physical properties that may be considered include, but are not limited to, viscosity versus shear rate, ease of application to surface, spreadability, and shear thinning.

V. Emulsion Polymerization to Make Latex Binder for Latex Paint

Emulsion polymerization is discussed in G. Pohlein, "Emulsion Polymerization", Encyclopedia of Polymer Science and Engineering, vol. 6, pp. 1-51 (John Wiley & Sons, Inc., NY, N.Y., 1986), the disclosure of which is incorporated herein by reference. Emulsion polymerization is a heterogeneous reaction process in which unsaturated monomers or monomer solutions are dispersed in a continuous phase with the aid of an emulsifier system and polymerized with free-radical or redox initiators. The product, a colloidal dispersion of the polymer or polymer solution, is called a latex.

The monomers typically employed in emulsion polymerization to make latex for latex paint include such monomers as methyl acrylate, ethyl acrylate, methyl methacrylate, butyl acrylate, 2-ethyl hexyl acrylate, other acrylates, methacrylates and their blends, acrylic acid, methacrylic acid, styrene, vinyl toluene, vinyl acetate, vinyl esters of higher carboxylic acids than acetic acid, e.g. vinyl versatate, acrylonitrile, acrylamide, butadiene, ethylene, vinyl chloride and the like, and mixtures thereof. This is further discussed below in the section entitled "Latex Monomers".

In the above process, suitable initiators, reducing agents, catalysts and surfactants are well known in the art of emulsion polymerization. Typical initiators include ammonium persulfate (APS), hydrogen peroxide, sodium, potassium or ammonium peroxydisulfate, dibenzoyl peroxide, lauryl peroxide, ditertiary butyl peroxide, 2,2'-azobisisobutyronitrile, t-butyl hydroperoxide, benzoyl peroxide, and the like. Commonly used redox initiation systems are described e.g., by A. S. Sarac in Progress in Polymer Science 24(1999), 1149-1204.

Suitable reducing agents are those which increase the rate of polymerization and include for example, sodium bisulfite, sodium hydrosulfite, sodium formaldehyde sulfoxylate, ascorbic acid, isoascorbic acid, and mixtures thereof.

Suitable catalysts are those compounds which increase the rate of polymerization and which, in combination with the above-described reducing agents, promote decomposition of the polymerization initiator under the reaction conditions. Suitable catalysts include transition metal compounds such as, for example, ferrous sulfate heptahydrate, ferrous chloride, cupric sulfate, cupric chloride, cobalt acetate, cobaltous sulfate, and mixtures thereof.

Emulsion polymerization occurs in the presence of an emulsifier. Typically the mixture contains 0.5 to 6 wt % emulsifier based on weight of latex monomers Typical emulsifiers are ionic or non-ionic surfactants polymerizable or non-polymerizable in the aqueous coating composition including latex polymer. Suitable ionic and nonionic surfactants are alkyl polyglycol ethers such as ethoxylation products of lauryl, tridecyl, oleyl, and stearyl alcohols; alkyl phenol polyglycol ethers such as ethoxylation products of octyl- or nonylphenol, diisopropyl phenol, triisopropyl phenol; alkali metal or ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The polymer latex binder can be produced by first preparing an initiator solution comprising the initiator and water. A monomer pre-emulsion is also prepared comprising one or more surfactants (emulsifiers), and other latex monomers to be used to form the latex polymer, water, and additional additives such as NaOH.

Thus, a typical process of emulsion polymerization preferably involves charging water to a reactor and feeding as separate streams a pre-emulsion of the monomer and a solution of the initiator. In particular, the polymer latex binder can be prepared using emulsion polymerization by feeding the monomers used to form the latex binder to a reactor in the presence of at least one initiator and at least one surfactant and polymerizing the monomers to produce the latex binder. Typically the initiator solution and monomer pre-emulsion are continuously added to the reactor over a predetermined period of time (e.g. 1.5-5 hours) to cause polymerization of latex monomers to produce the latex polymer.

Prior to the addition of the initiator solution and the monomer pre-emulsion, a seed latex such as a polystyrene seed latex can be added to the reactor. For example, a small amount of the pre-emulsion and a portion of the initiator may be charged initially at the reaction temperature to produce "seed" latex. The "seed" latex procedure results in better particle-size reproducibility.

Under "normal" initiation conditions, that is initiation conditions under which the initiator is activated by heat, the polymerization is normally carried out at about 60-90° C. A typical "normal" initiated process, for example, could employ ammonium persulfate as initiator at a reaction temperature of 80+/−2° C. Under "redox" initiation conditions, namely initiation conditions under which the initiator is activated by a reducing agent, the polymerization is normally carried out at 60-70° C. Normally, the reducing agent is added as a separate solution. A typical "redox" initiated process, for example, could employ potassium persulfate as the initiator and sodium metabisulfite as the reducing agent at a reaction temperature of 65+/−2° C.

The reactor is operated at desired reaction temperature at least until all the monomers are fed to produce the polymer latex binder. Once the polymer latex binder is prepared, it is preferably chemically stripped thereby decreasing its residual monomer content. Preferably, it is chemically stripped by continuously adding an oxidant such as a peroxide (e.g. t-butylhydroperoxide) and a reducing agent (e.g. sodium acetone bisulfite), or another redox pair such as those described by A. S. Sarac in Progress in Polymer Science 24(1999), 1149-1204, to the latex binder at an elevated temperature and for a predetermined period of time (e.g. 0.5 hours). The pH of the latex binder can then be adjusted and other additives added after the chemical stripping step.

In the above emulsions, the polymer preferably exists as a generally spherical particle, dispersed in water, with a diameter of about 50 nanometers to about 500 nanometers.

For purposes of this description, monomers from which latex polymers may be derived are termed "latex monomers".

The latex monomers fed to a reactor to prepare the polymer latex binder preferably include at least one acrylic monomer selected from the group consisting of acrylic acid, acrylic acid esters, methacrylic acid, and methacrylic acid esters. In addition, the monomers can include styrene, vinyl acetate, or ethylene. The monomers can also include one or more monomers selected from the group consisting of styrene, (alpha)-methyl styrene, vinyl chloride, acrylonitrile, methacrylonitrile, ureido methacrylate, vinyl acetate, vinyl esters of branched tertiary monocarboxylic acids (e.g. vinyl esters commercially available under the mark VEOVA from Shell Chemical Company or sold as EXXAR neo vinyl esters by ExxonMobil Chemical Company), itaconic acid, crotonic acid, maleic acid, fumaric acid, and ethylene. It is also possible to include C4-C8 conjugated dienes such as 1,3-butadiene, isoprene or chloroprene. Commonly used monomers in making acrylic paints are butyl acrylate, methyl methacrylate, ethyl acrylate and the like. Preferably, the monomers include one or more monomers selected from the group consisting of n-butyl acrylate, methyl methacrylate, styrene and 2-ethylhexyl acrylate.

The latex polymer is typically selected from the group consisting of pure acrylics (comprising acrylic acid, methacrylic acid, an acrylate ester, and/or a methacrylate ester as the main monomers); styrene acrylics (comprising styrene and acrylic acid, methacrylic acid, an acrylate ester, and/or a methacrylate ester as the main monomers); vinyl acrylics (comprising vinyl acetate and acrylic acid, methacrylic acid, an acrylate ester, and/or a methacrylate ester as the main monomers); and acrylated ethylene vinyl acetate copolymers (comprising ethylene, vinyl acetate and acrylic acid, methacrylic acid, an acrylate ester, and/or a methacrylate ester as the main monomers). The monomers can also include other main monomers such as acrylamide and acrylonitrile, and one or more functional monomers such as itaconic acid and ureido methacrylate, as would be readily understood by those skilled in the art. In a particularly preferred embodiment, the latex polymer is a pure acrylic such as a butyl acrylate/methyl methacrylate copolymer derived from monomers including butyl acrylate and methyl methacrylate.

In typical acrylic paint compositions the polymer is comprised of one or more esters of acrylic or methacrylic acid, typically a mixture, e.g. about 50/50 by weight, of a high $T_g$ monomer (e.g. methyl methacrylate) and a low $T_g$ monomer (e.g. butyl acrylate), with small proportions, e.g. about 0.5% to about 2% by weight, of acrylic or methacrylic acid. The vinyl-acrylic paints usually include vinyl acetate and butyl acrylate and/or 2-ethyl hexyl acrylate and/or vinyl versatate. In vinyl-acrylic paint compositions, at least 50% of the polymer formed is comprised of vinyl acetate, with the remainder being selected from the esters of acrylic or methacrylic acid. The styrene/acrylic polymers are typically similar to the acrylic polymers, with styrene substituted for all or a portion of the methacrylate monomer thereof.

The latex polymer dispersion preferably includes from about 30 to about 75% solids and a mean latex particle size of from about 70 to about 650 nm. The latex polymer is preferably present in the aqueous coating composition in an amount from about 5 to about 60 percent by weight, and more preferably from about 8 to about 40 percent by weight (i.e. the weight percentage of the dry latex polymer based on the total weight of the coating composition).

The aqueous coating composition is a stable fluid that can be applied to a wide variety of materials such as, for example, paper, wood, concrete, metal, glass, ceramics, plastics, plaster, and roofing substrates such as asphaltic coatings, roofing felts, foamed polyurethane insulation; or to previously painted, primed, undercoated, worn, or weathered substrates. The aqueous coating composition of the invention can be applied to the materials by a variety of techniques well known in the art such as, for example, brush, rollers, mops, air-assisted or airless spray, electrostatic spray, and the like.

V. Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component.

Thus, the term includes water per se as well as aqueous solutions and dispersions.

VI. Other Additives

As described above, latex paints and coatings may contain various adjuvants.

The aqueous coating compositions of the invention include less than 2% by weight and preferably less than 1.0% by weight of anti-freeze agents based on the total weight of the aqueous coating composition. For example, the aqueous coating compositions may be substantially free of anti-freeze agents.

The aqueous coating composition typically includes at least one pigment. The term "pigment" as used herein includes non-film-forming solids such as pigments, extenders, and fillers. The at least one pigment is preferably selected from the group consisting of TiO2 (in both anastase and rutile forms), clay (aluminum silicate), CaCO3 (in both ground and precipitated forms), aluminum oxide, silicon dioxide, magnesium oxide, talc (magnesium silicate), barytes (barium sulfate), zinc oxide, zinc sulfite, sodium oxide, potassium oxide and mixtures thereof. Suitable mixtures include blends of metal oxides such as those sold under the marks MINEX (oxides of silicon, aluminum, sodium and potassium commercially available from Unimin Specialty Minerals), CELITES (aluminum oxide and silicon dioxide commercially available from Celite Company), ATOMITES (commercially available from English China Clay International), carbon black, and ATTAGELS (commercially available from Engelhard). More preferably, the at least one pigment includes TiO2, CaCO3 or clay. Generally, the mean particle sizes of the pigments range from about 0.01 to about 50 microns. For example, the TiO2 particles used in the aqueous coating composition typically have a mean particle size of from about 0.15 to about 0.40 microns. The pigment can be added to the aqueous coating composition as a powder or in slurry form. The pigment is preferably present in the aqueous coating composition in an amount from about 5 to about 50 percent by weight, more preferably from about 10 to about 40 percent by weight.

The coating composition can optionally contain additives such as one or more film-forming aids or coalescing agents. Suitable firm-forming aids or coalescing agents include plasticizers and drying retarders such as high boiling point polar solvents. Other conventional coating additives such as, for example, dispersants, additional surfactants (i.e. wetting agents), rheology modifiers, defoamers, thickeners, additional biocides, additional mildewcides, colorants such as colored pigments and dyes, waxes, perfumes, co-solvents, and the like, can also be used in accordance with the invention. For example, non-ionic and/or ionic (e.g. anionic or cationic) surfactants can be used to produce the polymer latex. These additives are typically present in the aqueous coating composition in an amount from 0 to about 15% by weight, more preferably from about 1 to about 10% by weight based on the total weight of the coating composition.

The aqueous coating composition typically includes less than 10.0% of anti-freeze agents based on the total weight of the aqueous coating composition. Exemplary anti-freeze agents include ethylene glycol, diethylene glycol, propylene glycol, glycerol (1,2,3-trihydroxypropane), ethanol, methanol, 1-methoxy-2-propanol, 2-amino-2-methyl-1-propanol, and FTS-365 (a freeze-thaw stabilizer from Inovachem Specialty Chemicals). More preferably, the aqueous coating composition includes less than 5.0% or is substantially free (e.g. includes less than 0.1%) of anti-freeze agents. Accordingly, the aqueous coating composition of the invention preferably has a VOC level of less than about 100 g/L and more preferably less than or equal to about 50 g/L.

The balance of the aqueous coating composition of the invention is water. Although much of the water is present in the polymer latex dispersion and in other components of the aqueous coating composition, water is generally also added separately to the aqueous coating composition. Typically, the aqueous coating composition includes from about 10% to about 85% by weight and more preferably from about 35% to about 80% by weight water. Stated differently, the total solids content of the aqueous coating composition is typically from about 15% to about 90%, more preferably, from about 20% to about 65%.

The coating compositions are typically formulated such that the dried coatings comprise at least 10% by volume of dry polymer solids, and additionally 5 to 90% by volume of non-polymeric solids in the form of pigments. The dried coatings can also include additives such as plasticizers, dispersants, surfactants, rheology modifiers, defoamers, thickeners, additional biocides, additional mildewcides, colorants, waxes, and the like, that do not evaporate upon drying of the coating composition.

Experiments

New pigment polymeric dispersant with higher efficiency and improved stability of the pigment concentration: Efficiency and optimum usage level of dispersant was determined by dispersant demand curve studies. The starting point formulation for demand curve varies depending on pigment. Typically, organic pigments can be evaluated at 40-50% pigment loading, while carbon blacks can vary from 10-50% pigment loading depending on their properties such as particle size and surface treatment.

The process was prepared as follows: as a starting point, prepare a formulation consisting of pigment, dispersant, defoamer, Deionized (DI) water, and base (if needed). Liquid ingredients were added, including a small amount of polymeric dispersant as described herein, to the grind pot and mixed at low speeds using a high shear (Cowles) disperser. After a homogeneous mixture has been obtained, pigment was slowly added. Once all of the pigment had been added, mixed at a maximum speed needed to create a strong vortex. After premix finished, attached cooling water, added milling beads and prepared for milling. After 30 minutes milling, waited one minute and measured the viscosity via Brookfield viscometer. Continued to add dispersant incrementally and milled for 4-6 minutes after each addition, and take the measurement for viscosity. Test completed when the viscosity shows significant increase.

Table I

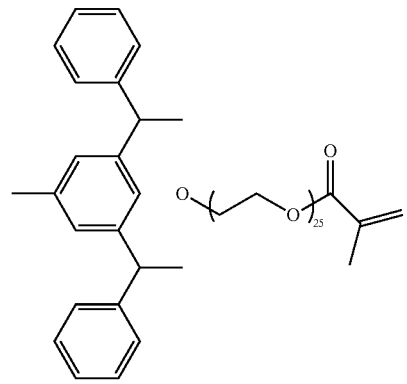

Distyryl Methyl Phenol-25 EO Methacrylate ($C_1$)

Table I-continued

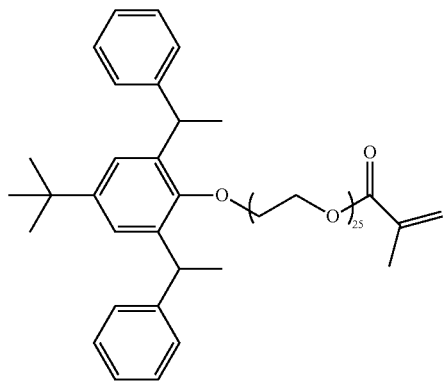

Distyryl t-Butyl Phenol-
25 EO Methacrylate
($C_4$)

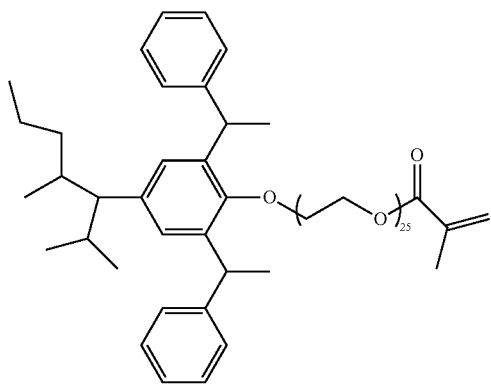

Distyryl Nonyl Phenol-
25 EO Methacrylate
($C_9$)

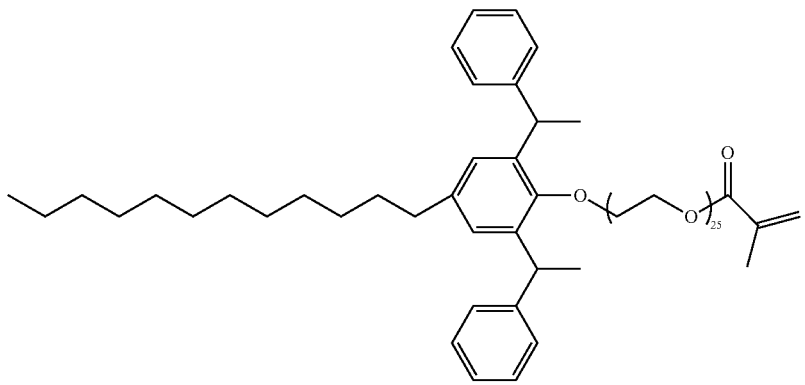

Distyryl Dodecyl Phenol-
25 EO Methacrylate
($C_{12}$)

Polymeric dispersants containing monomers reported on Table I were evaluated. The polymers with different DSP-ethoxylate methacrylate monomers were prepared by emulsion polymerization were first neutralized to pH 8-9 with ammonia then were evaluated as dispersant. The efficiency and optimum usage level of the dispersant was tested by demand curve study by following the procedure previously described, as shown in FIG. 1. Raven 5000 carbon black was used for this study.

Referring to FIG. 1, based on the dispersant demand curve studies, the dispersants developed by the present invention showed improved efficiency to disperse pigment as compared to commercial polymeric dispersant (competitive 1—Tego 755W). It was observed that the optimized usage level of dispersant of the present invention is about 35% active based on dry pigment, as compared to the recommended usage level by competitive 1, which is about 60% (as recommended by supplier).

The pigment concentration was prepared according to the following procedure:

Added DI water, dispersant, defoamer, and ammonia to the grind pot and mixed well. Formulas to prepare the pigment concentration are given in Table II. Pigment powder was the added to the grind pot slowly under agitation at a low speed using a high shear (Cowles) disperser. After the pigment was been added, mixed at high speed for 20 minutes. After premix finished, attached cooling water, added milling beads and prepared for milling for 60 minutes or until the desired color strength and coloristic properties were obtained.

TABLE II

Pigment concentration preparation

| Raw materials | Competitive 1 | DP-1 ($C_1$) | DP-2 ($C_4$) | DP-3 ($C_9$) | DP-4 ($C_{12}$) |
|---|---|---|---|---|---|
| DI Water | 118.5 | 106 | 106 | 106 | 106 |
| Defoamer | 2.5 | 2.5 | 2.5 | 2.5 | 2.5 |
| Ammonia | 4 | 4 | 4 | 4 | 4 |
| Competitve 1 (40%) | 75 | | | | |
| DP-1 (20%) | | | 87.5 | | |
| DP-2 (20%) | | | | | 87.5 |
| DP-3 (20%) | | 87.5 | | | |
| DP-4 (20%) | | | | 87.5 | |
| Raven 5000 Ultra II pigment | 50 | 50 | 50 | 50 | 50 |
| Total | 250 | 250 | 250 | 250 | 250 |
| % Dispersant (solids on pigment) | 60% | 35% | 35% | 35% | 35% |
| % Carbon Black pigment | 20% | 20% | 20% | 20% | 20% |

The pigment concentration prepared by the polymeric dispersant polymers of the present invention showed very low initial viscosity, and also were much more stable on storage compared to the commercial competitive 1 dispersant.

TABLE III

Properties of pigment concentration.

| Properties | Competitive 1 | DP-1 ($C_1$) | DP-2 ($C_4$) | DP-3 ($C_9$) | DP-4 ($C_{12}$) |
|---|---|---|---|---|---|
| Initial results | | | | | |
| Particle size (d · nm) | 111.3 | 109.4 | 107.3 | 112 | 112.5 |
| pH | 8.63 | 8.88 | 8.91 | 8.4 | 8.43 |
| Viscosity, 12 RPM | 50 | 50 | 40 | 40 | 60 |
| Viscosity, 60 RPM | 50 | 56 | 74 | 86 | 52 |
| Viscosity, 100 RPM | 31.2 | 61.2 | 79.2 | 87.6 | 52.8 |
| Results after 7 day heat-aging | | | | | |
| pH | 7.7 | 8.07 | 8.21 | 7.83 | 7.71 |
| Viscosity, 12 RPM | 34592 | 1110 | 739.8 | 80 | 10 |
| Viscosity, 60 RPM | N/A | 937.8 | 659.9 | 120 | 50 |
| Viscosity, 100 RPM | N/A | 839.8 | 610.7 | 94.8 | 58.8 |
| Particle size (d · nm) | 163 | 152.5 | 131.2 | 114.9 | 110.7 |

The pigment concentration prepared by the polymeric dispersant polymers of the present invention showed good compatibility to various types of paints and coatings. It showed excellent color strength development compared to the standard dispersion. The jetness and L value, as well as run-up test were also comparable in comparison the standard the dispersion.

TABLE 3

Properties of paints tinted with the pigment concentration.

Tinting results for gloss acrylic deepbase (12% w/w)

| Properties (measured after 7 days) | Competitive 1 | DP-1 ($C_1$) | DP-2 ($C_4$) | DP-3 ($C_9$) | DP-4 ($C_{12}$) |
|---|---|---|---|---|---|
| Masstone color strength | 100% | 102.34% | 103.33% | 102.51% | 103.24% |
| L* | 24.62 | 24.29 | 24.18 | 24.22 | 24.24 |
| B* | −0.41 | −0.34 | −0.36 | −0.36 | −0.34 |
| Y* | 4.29 | 4.19 | 4.16 | 4.18 | 4.23 |

TABLE 3-continued

| Properties of paints tinted with the pigment concentration. | | | | | |
|---|---|---|---|---|---|
| My value (jetness) | 136.8 | 137.8 | 138.1 | 137.9 | 137.4 |
| Gloss 20° | 63.3 | 57.9 | 57.2 | 50.2 | 52.8 |
| Gloss 60° | 86.1 | 83.2 | 82.7 | 82.6 | 80.6 |

Tinting results for clear 1K PU coating (8.5% w/w)

| Properties | Competitive 1 | DP-1 ($C_1$) | DP-2 ($C_4$) |
|---|---|---|---|
| Masstone color strength | 100% | 99.61% | 99.88% |
| L* | 24.38 | 24.42 | 24.44 |
| B* | 0.05 | 0 | −0.01 |
| Y* | 4.23 | 4.24 | 4.24 |
| My value (jetness) | 137.4 | 137.3 | 137.3 |
| Gloss 20° | 47.2 | 46.9 | 47.5 |
| Gloss 60° | 78.3 | 78.6 | 78.4 |

Tinting results for gloss acrylic white paint (2%, w/w)

| Properties | Competitive 1 | DP-1 ($C_1$) | DP-2 ($C_4$) | |
|---|---|---|---|---|
| Tint strength | 100% ctrl | 98.30% | 98.50% | 93.00% |
| Rub up ΔE | 0.26 | 0.17 | 0.15 | 0.2 |

It should be apparent embodiments other than those expressly described above come within the spirit and scope of the present invention. Thus, the present invention is not defined by the above description but by the claims appended hereto.

What is claimed is:

1. A polymeric dispersant comprising at least one monomer according to structure D.XVI:

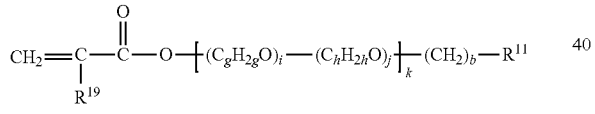

(D.XVI)

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is according to structure D.XII

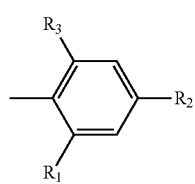

D.XII wherein $R_1$, $R_2$ and $R_3$ are independently selected from the following structures D.XIIIa, D.XIIIb, D.XIIIc, D.XIIId:

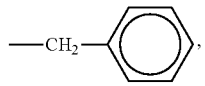 D.XIIIa

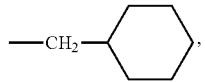 D.XIIIb

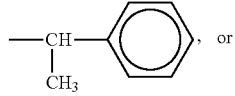 D.XIIIc

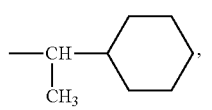 D.XIIId or a $C_5$-$C_{30}$ branched or linear alkyl group or alkenyl group; wherein at least one of $R_1$, $R_2$ and $R_3$ is the $C_5$-$C_{30}$ branched or linear alkyl group or alkenyl group and at least one of $R_1$, $R_2$ and $R_3$ is selected from structure D.XIIIa, D.XIIIb, D.XIIIc, or D.XIIId; and
wherein the polymeric dispersant has a weight average molecular weight of between 2,000 g/mole to 25,000 g/mole.

2. The polymeric dispersant of claim 1 wherein the weight average molecular weight is between 2,000 g/mole to 15,000 g/mole.

3. The polymeric dispersant of claim 1 wherein the $C_5$-$C_{30}$ branched or linear alkyl group or alkenyl group is a $C_9$-$C_{30}$ branched or linear alkenyl group.

4. The polymeric dispersant of claim 1 wherein the $C_5$-$C_{30}$ branched or linear alkyl group or alkenyl group is a $C_6$-$C_{14}$ branched or linear alkyl group.

5. The polymeric dispersant of claim 1 wherein the $C_5$-$C_{30}$ branched or linear alkyl group or alkenyl group is a $C_9$-$C_{14}$ branched or linear alkenyl group.

6. The polymeric dispersant of claim 1 wherein the $C_5$-$C_{30}$ branched or linear alkyl group or alkenyl group is a $C_8$-$C_{12}$ branched or linear alkyl group.

7. The polymeric dispersant of claim 1 wherein the $C_5$-$C_{30}$ branched or linear alkyl group or alkenyl group is a $C_{23}$-$C_{30}$ branched or linear alkenyl group.

8. The polymeric dispersant of claim 1 wherein $R^{11}$ is a tri-substituted aromatic group according to the structure D.XII

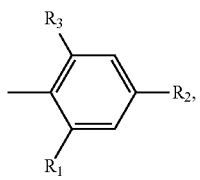

D.XII wherein $R_1$, $R_2$ and $R_3$ are independently selected from:
a styryl group, or
a $C_5$-$C_{30}$ branched or linear alkyl group or alkenyl group; wherein at least one of $R_1$, $R_2$ and $R_3$ is the $C_5$-$C_{30}$ branched or linear alkyl group or alkenyl group, and at least one of $R_1$, $R_2$ and $R_3$ is the styryl group.

9. The polymeric dispersant of claim 1 wherein $R^{11}$ is a tri-substituted aromatic group according to the structure D.XII-1

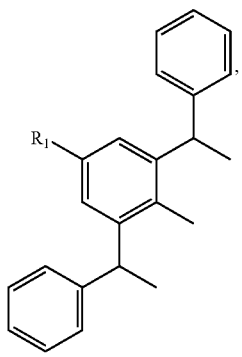

D.XII-1 wherein $R_1$, is the $C_5$-$C_{30}$ branched or linear alkyl group or alkenyl group.

10. The polymeric dispersant of claim 1 wherein the polymeric dispersant is characterized as an oligomer.

11. A polymeric dispersant copolymer, comprising, based on total weight of monomers:
A. about 0-60 weight percent of the at least one $C_3$-$C_8$ alpha beta-ethylenically unsaturated acidic monomer, preferably a $C_3$-$C_8$ alpha beta-ethylenically unsaturated carboxylic acid monomer;
B. about 15-70 weight percent of the at least one nonionic, copolymerizable $C_2$-$C_{12}$ alpha, beta-ethylenically unsaturated monomer; and
C. about 0.01-30 weight percent of the at least one ethylenically unsaturated hydrophobic monomer according to structure D.XVI:

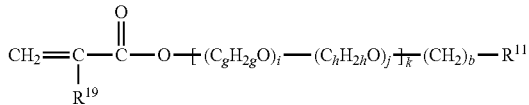

(D.XVI)

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is a tri-substituted aromatic group according to the structure D.XII

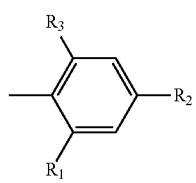

D.XII wherein $R_1$, $R_2$ and $R_3$ are independently selected from the following structures D.XIIIa, D.XIIIb, D.XIIIc, D.XIIId:

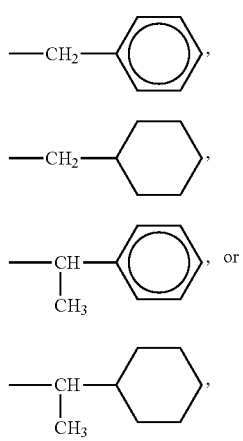

D.XIIIa

D.XIIIb

D.XIIIc

D.XIIId or a $C_5$-$C_{30}$ branched or linear alkyl group or alkenyl group; wherein at least one of $R_1$, $R_2$ and $R_3$ is the $C_5$-$C_{30}$ branched or linear alkyl group or alkenyl group and at least one of $R_1$, $R_2$ and $R_3$ is selected from structure D.XIIIa, D.XIIIb, D.XIIIc, or D.XIIId; and
wherein the polymeric dispersant has a weight average molecular weight of between 2,000 g/mole to 25,000 g/mole.

12. The polymeric dispersant copolymer of claim 11 wherein the weight average molecular weight is between 2,000 g/mole to 15,000 g/mole.

13. The polymeric dispersant copolymer of claim 11 wherein the carboxylic acid monomer (A) is present from about 15 weight percent to about 60 weight percent based on total monomer weight.

14. The polymeric dispersant copolymer of claim 11 wherein the carboxylic acid monomer (A) is selected from a group consisting of methacrylic acid, acrylic acid and a combination thereof.

15. The polymeric dispersant copolymer of claim 11 wherein the nonionic monomer (B) is alkyl acrylate.

16. A method for dispersing pigments in an aqueous emulsion, comprising: contacting (i) an aqueous emulsion containing at least one pigment with
(ii) a polymeric dispersant copolymer, comprising, based on total weight of monomers:
  A. about 0-60 weight percent of the at least one $C_3$-$C_8$ alpha beta-ethylenically unsaturated acidic monomer, preferably a $C_3$-$C_8$ alpha beta-ethylenically unsaturated carboxylic acid monomer;
  B. about 15-70 weight percent of the at least one non-ionic, copolymerizable $C_2$-$C_{12}$ alpha, beta-ethylenically unsaturated monomer; and
  C. about 0.01-30 weight percent of the at least one ethylenically unsaturated hydrophobic monomer according to structure D.XVI:

(D.XVI)

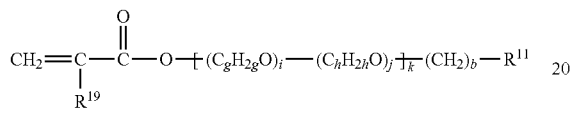

wherein:
g is an integer from 2 to 4;
h is an integer from 2 to 4;
b is an integer from 0 to 1;
k is an integer from 0 to 25;
i is an integer from 0 to 40;
j is an integer from 0 to 40;
$R^{19}$ is hydrogen; methyl or ethyl;
$R^{11}$ is a tri-substituted aromatic group according to the structure D.XII

D.XII

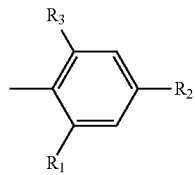

wherein $R_1$, $R_2$ and $R_3$ are independently selected from the following structures D.XIIIa, D.XIIIb, D.XIIIc, D.XIIId:

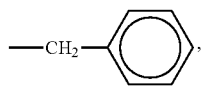

D.XIIIa

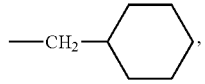

D.XIIIb

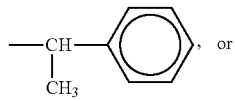

D.XIIIc

, or

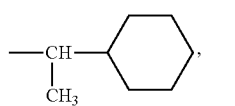

D.XIIId or a $C_5$-$C_{30}$ branched or linear alkyl group or alkenyl group;
wherein at least one of $R_1$, $R_2$ and $R_3$ is the $C_2$-$C_{30}$ branched or linear alkyl group or alkenyl group and at least one of $R_1$, $R_2$ and $R_3$ is selected from structure D.XIIIa, D.XIIIb, D.XIIIc, or D.XIIId; and
wherein the polymeric dispersant has a weight average molecular weight of between 2,000 g/mole to 25,000 g/mole.

17. The method of claim 16 wherein the pigment is carbon black.

18. The method of claim 16 wherein the weight average molecular weight of the polymeric dispersant copolymer is between 2,000 g/mole to 15,000 g/mole.

19. The method of claim 16 wherein the $C_5$-$C_{30}$ branched or linear alkyl group or alkenyl group is a $C_9$-$C_{30}$ branched or linear alkenyl group.

20. The method of claim 16 wherein the $C_5$-$C_{30}$ branched or linear alkyl group or alkenyl group is a $C_6$-$C_{14}$ branched or linear alkyl group.

* * * * *